US008395131B2

(12) United States Patent
Wu et al.

(10) Patent No.: US 8,395,131 B2

(45) Date of Patent: Mar. 12, 2013

(54) METHOD FOR THREE DIMENSIONAL (3D) LATTICE RADIOTHERAPY

(76) Inventors: Xiaodong Wu, Miami, FL (US); Mansoor M. Ahmed, Miami, FL (US); Alan Pollack, Miami, FL (US)

(*) Notice: Subject to any disclaimer, the term of this patent is extended or adjusted under 35 U.S.C. 154(b) by 20 days.

(21) Appl. No.: 12/819,212

(22) Filed: Jun. 20, 2010

(65) Prior Publication Data

US 2010/0320402 A1 Dec. 23, 2010

Related U.S. Application Data

(60) Provisional application No. 61/218,928, filed on Jun. 20, 2009.

(51) Int. Cl.
*A61N 5/10* (2006.01)

(52) U.S. Cl. .......................... 250/492.1; 372/64; 372/65

(58) Field of Classification Search ............... 250/492.1; 378/64–65; 606/2.5
See application file for complete search history.

(56) References Cited

U.S. PATENT DOCUMENTS

| | | | | |
|---|---|---|---|---|
| 5,027,818 | A * | 7/1991 | Bova et al. | 600/427 |
| 7,317,192 | B2 * | 1/2008 | Ma | 250/492.1 |
| 2004/0227104 | A1 * | 11/2004 | Matsuda et al. | 250/492.1 |
| 2006/0239404 | A1 * | 10/2006 | Udpa et al. | 378/62 |
| 2007/0053490 | A1 * | 3/2007 | Wang et al. | 378/65 |
| 2007/0286343 | A1 * | 12/2007 | Maciunas et al. | 378/65 |
| 2010/0056908 | A1 * | 3/2010 | Giller et al. | 378/65 |
| 2010/0104068 | A1 * | 4/2010 | Kilby et al. | 378/65 |
| 2011/0108737 | A1 * | 5/2011 | Pu et al. | 250/398 |
| 2011/0206252 | A1 * | 8/2011 | Eriksson Jarliden | 382/128 |
| 2011/0272600 | A1 * | 11/2011 | Bert et al. | 250/492.1 |
| 2012/0020460 | A1 * | 1/2012 | Witten et al. | 378/65 |

OTHER PUBLICATIONS

Brown WT,WU X, Amendola B, Perman M, Han H, Fayad F, Garcia S, Lewin A, Abitol A, De La Zerda A and Schwade JG, Treatment of Early Non-small cell lung cancer, Stage 1A, by Image-guided Robotic Stereotactic Radioblation—Cyberknife, The Cancer Journal 13(2) pp. 87-94, (2007).

Crooks SM, Wu X, Takita C, Watzich M and Xing L, Aperture Modulated Arc Therapy, Phys. Med. Biol. 48 pp. 1333-1344 (2003).

Freid JR, Lipman A, Jacobson LE, Roentgen Therapy through a Grid for Advanced Carcinoma, Amer. J. Roentgen 70 p. 460 (1953).

Liberson F, The Value of a Multi-perforated Screen in Deep X-ray Thereapy, Radiology 20 p. 186-195 (1933).

(Continued)

*Primary Examiner* — David A Vanore

*Assistant Examiner* — Wyatt Stoffa

(74) *Attorney, Agent, or Firm* — Pinkert & Marsh, P.A.; Steven Pinkert, Esq.; Calrie Marsh, Esq.

(57) ABSTRACT

A method for high-dose Grid radiotherapy utilizing a three-dimensional (3D) dose lattice formation is described herein. The 3D dose lattice can be achieved by, but not limited to, three technical approaches: 1) non-coplanar focused beams; 2) multileaf collimator (MLC)-based intensity modulated radiation therapy (IMRT) or aperture-modulated arc; and 3) heavy charged particle beam. The configuration of a 3D dose lattice is comprised of the number, location, and dose of dose vertices. The optimal configuration of a 3D dose lattice can be achieved by manual calculations or by automating the calculations for a generic algorithm. The objective of the optimization algorithm is to satisfy three conditions via iteration until they reach their global minimum. With 3D dose lattice, high doses of radiation are concentrated at each lattice vertex within a tumor with drastically lower doses between vertices (peak-to-valley effect), leaving tissue outside of the tumor volume minimally exposed.

2 Claims, 11 Drawing Sheets

420 405 415 410 411 400

OTHER PUBLICATIONS

Marks H, Clinical Experience with Irradiation through a GRID, Radiology 58 pp. 338-342 (1952).
Mohiuddin M, Fujita M, Regine W F, Megooni A S, Iboot G S, Ahmed M M, High-dose Spatially Fractionated Radiation (GRID): A new paradigm in the management of advanced cancer, Int. J. Radiat. Oncol. Biol. Phys. 45 pp. 721-727 (1999).
Neuner G A, Vander Walde N, Ha J K, Yu C X and Mohiuddin M High-dose Spatially-Fractionated GRID Radiation Therapy (SFGRT): A comparison of outcomes of treatment delivered through Cerrobend GRID versus MLC GRID, Int. J. Radiat. Oncol. Biol. Phys. 72S p. 488 (2008).
Peters M E, Shareef M M, Gupta S, Zagurovskaya-Sultanov M, Kadhim M, Mohiuddin M and Ahmed M M, Potential Utilization of Bystander / Abscopal-Mediated Signal Transduction Events in the Treatment of Solid Tumors, Current Signal Transduction Thereapy 2(2) pp. 129-143 (2007).
Sathishkumar S, Boyanovsky B, Karakashian A A, Rozenova K, Giltiay N V, Kudrimoti M, Mohiuddin M, Ahmed M M and Nikolova-Karakashian M, Elevated Sphingomyelinase Activity and Ceramide Concentration in Serum of Patients Undergoing High Dose Spatially Fractionated Radiation Treatment: Implications for Endothelial Apoptosis, Cancer Biol. Ther. 4(9) pp. 979-986 (2005).
Sathishkumar S, Dey S, Meigooni AS, Regine W F, Kudrimoti M S, Ahmed M M and Mohiuddin M, The Impact of TNF-alpha Induction on Therapeutic Efficacy Following High Dose Spatially Fractionated (GRID) Radiation, Technology in Cancer Research Treatment 1(2) pp. 114-147 (2002).
Shareef M M, Cui N, Burikhanov R, Gupta S, Sathishkumar S, Shajahan S, Mohiuddin M, Rangnekar V M and Ahmed M M, Role of TNF-α and TRAIL in High Dose Radiation-induced Bystander Signaling in Lung Adenocarcinoma, Cancer Research 67 (24) pp. 11811-11820 (2007).
Shulz-Ertner D, Tsujii H, Particle Therapy Using Proton and Heavier Ion Beams, J. Clin. Oncol. 25 pp. 953-964, (2007).
Zwicker RD, Meigoonia, Mohiuddin M, Therapeutic Advantage of GRID Irradiation for Large Single Fractions, Int. J. Radiat. Oncol. Biol. Phys. 58 pp. 1309-1315 (2004).

* cited by examiner

METHOD FOR THREE DIMENSIONAL (3D) LATTICE RADIOTHERAPY

CROSS-REFERENCE TO RELATED APPLICATIONS

This application claims the benefit of U.S. Provisional Application No. 61/218,928 filed Jun. 20, 2009. The entire disclosure of this prior application is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

The present invention relates generally to high-dose Grid radiotherapy.

BACKGROUND

High-dose Grid radiotherapy, or sometimes termed spatially-fractionated Grid radiotherapy (SFGRT), was first introduced in the early 1930's. It has remained a less frequently used treatment modality since its inception and practice. Early applications of high-dose Grid radiotherapy used two-dimensional (2D) Grid fields, typically with orthovoltage beams allowing spatially alternated dose distributions. The Grids were usually composed of open/shield circular or square shapes ranging in size from 0.5 cm to 1.5 cm. The application was mainly for the treatment of advanced bulky tumors. It was proposed that such treatment technique permits higher dose delivery with acceptable skin toxicity because highly exposed skin regions are surrounded by undamaged skin resulting in improved repair to those exposed skin regions. With this technique, only a portion of the tumor volume receives therapeutic dose.

Although relatively small numbers of patients have received Grid treatment either with orthovoltage or more recently with MV X-rays, significant and dramatic tumor regressions have been observed and reported even though Grid therapy, in contradistinction to conventional approaches, does not attempt to treat the total tumor volume with a rather uniform dose.

Recent research in radiobiology has brought forth newly revealed biological insights. These include the bystander effect within the Grid irradiated tumor volume that occurs in the tumor cells that fall directly under shielded regions (low-dose regions) of the Grid. Bystander factors such as Tumor Necrosis Factor-$\alpha$ (TNF-$\alpha$), TNF-Related Apoptosis-Inducing Ligand (TRAIL), and Ceramide are induced in cells that are under the open field of the high-dose Grid areas and are hypothesized to be responsible for initiating the cell death cascade both in the epithelial and endothelial compartments of the tumor micro-environment. In addition to the bystander effect within the Grid irradiated tumor, robust abscopal effect in distant tumors or metastatic lesions that are not irradiated or treated has been reported. This data from radiobiology research conducted strongly suggests that Grid therapy induces a more rapid rate of tumor cell apoptosis in bulky, hypoxic, tumors than conventional dosimetric approaches. It is hypothesized from the research results that induction high-dose Grid radiotherapy would enhance the therapeutic outcome of subsequent chemotherapy or conventional radiation therapy.

SUMMARY

The present invention teaches a method of high-dose Grid radiotherapy by utilizing a 3D dose lattice formation. Although effective with acceptable toxicity, 2D Grid field treatments still expose high doses of radiation to a considerable volume of normal tissue. This high dose exposure to the surrounding normal tissue can be significantly reduced by reconfiguring the Grid treatment into a three-dimensional (3D) dose lattice, which is the aim and advantage of the present invention. With 3D dose lattice, high doses of radiation are concentrated at each lattice vertex within the tumor volume, with drastically lower doses between vertices (peak-to-valley effect) and leaving tissue outside of the tumor volume minimally exposed.

The term "lattice" is used here figuratively and not for purposes of implying or expressing any rigorous requirement of symmetry. The 3D dose lattice can be achieved by, but not limited to, three technical approaches: 1) non-coplanar focused beams; 2) multileaf collimator (MLC)-based intensity modulated radiation therapy (IMRT) or aperture-modulated arc; and 3) heavy charged particle beam. The treatment planning to achieve optimal lattice dose distribution using these three technical approaches can be done manually or via automation. The three technical approaches and both manual and automatic generation of the 3D dose lattice formation are disclosed herein as embodiments of the present invention.

2D Grid therapies have been offered to many patients with advanced and bulky tumors, for whom, there would have been otherwise no possible treatment options. The 2D Grid therapy requires the manufacture of a Grid block, whereas the 3D dose lattice radiotherapy (LRT) technique described herein does not require the manufacture of a Grid block. In addition the 3D dose lattice radiotherapy described herein offers less toxicity and therefore is applicable to more patients. Additionally, if the therapeutic role of bystander effect is demonstrated clinically, a new paradigm of using high-dose (for example 10 Gy and higher) 3D lattice radiation as induction therapy followed by conventional radiation therapy or chemotherapy can be anticipated.

The basic principle of the lattice radiotherapy is to create, within tumor volume, multiple localized high-dose regions (for example 10 Gy and higher) with a certain degree of separation to form low dose regions (for example 3 Gy and lower) between vertices and with minimized dose outside of the tumor volume. It should be noted that the vertex dose distribution needs not be spherical or near spherical. In certain cases, a single focused dose vertex could be introduced in a small tumor. The present invention as disclosed herein improves upon this basic principle and would achieve optimal treatment benefits with a significant reduction in the currently acceptable toxicity to the surrounding tissue.

BRIEF DESCRIPTION OF THE DRAWINGS

In describing the invention, reference will at times be made to the accompanying drawings in which:

FIG. 1A illustrates the 2D Grid radiation field. FIG. 1B shows the 3D dose lattice formation with focused photon beams.

FIG. 2A shows the dose lattice formation with 11 dose vertices. FIG. 2B shows a coronal plane view of the isodose distribution to the tumor volume and the associated peak-valley profile line.

FIG. 3A shows 13 dose vertices delivered in one aperture-modulated arc.

FIG. 3B shows a coronal plane view of the isodose distribution to the lung tumor and the associated peak-to-valley profile line.

DESCRIPTION OF INVENTION

Before the subject invention is described further, it is to be understood that the invention is not limited to the particular embodiments of the invention described below, as variations of the particular embodiments may be made and still fall within the scope of the invention. It is also to be understood that the terminology employed is for the purpose of describing particular embodiments, and is not intended to be limiting.

The details of one or more embodiments of the invention are set forth in the accompanying drawings and the description below. Other features, objects, and advantages of the invention will be apparent from the description and drawings, and from the claims. In the following description, numerous specific details are set forth to provide a thorough understanding of the embodiments. One skilled in the art to which this invention belongs will recognize, however, that the techniques described can be practiced without one or more of the specific details, or with other methods, components, materials, etc. In other instances, well known structures, materials or operations are not shown or described in detail to avoid obscuring certain aspects.

In this specification, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

The term "lattice" is used herein figuratively and not for purposes of implying or expressing any rigorous requirement of symmetry or geometry.

The term "dose lattice" is used herein to mean a three-dimensional (3D) dose distribution consisting of multiple discrete high dose regions in three dimensions surrounded by low dose regions on all sides of the high dose regions.

The term "dose vertex" is used herein to mean the discrete high dose region in the dose lattice. The term "dose vertices" is used herein as the plural reference for "dose vertex".

Figure 1A:
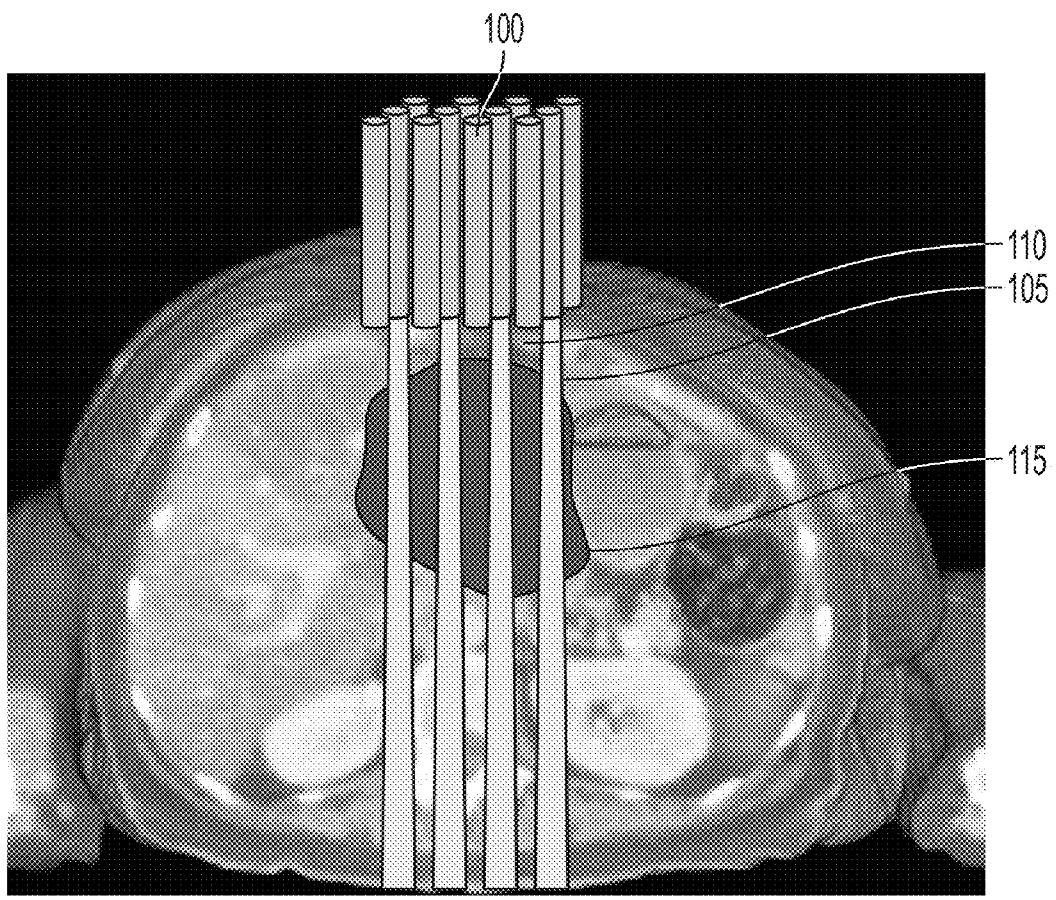
FIGS. 1A and 1B illustrate the conceptual comparison/difference between the traditional 2D Grid radiation treatment and the 3D dose lattice radiation treatment.
Figure 1B:
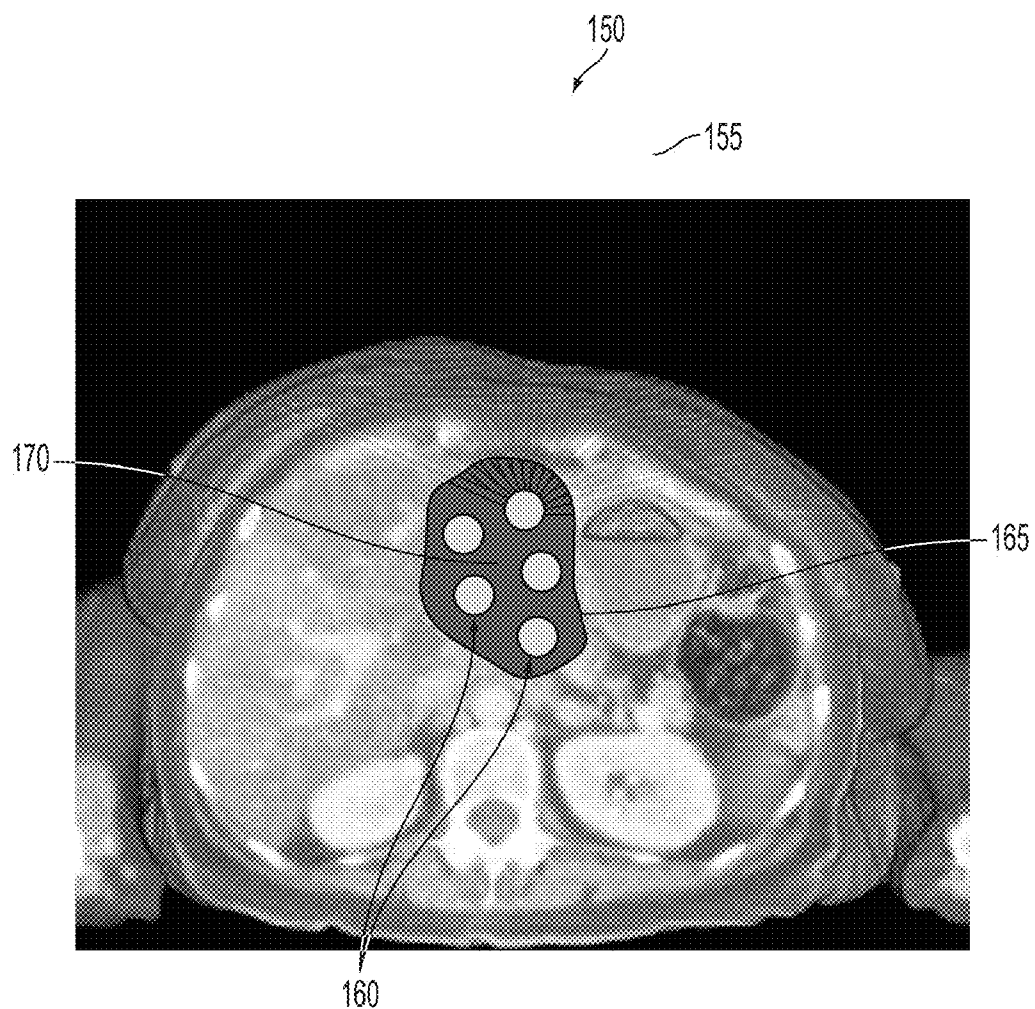

FIGS. 1A and 1B respectively show a conceptual comparison between the traditional 2D Grid radiation therapy and the 3D dose lattice formation with focused photon beams. FIG. 1A shows the 2D Grid radiation block 100 where the radiation beams 105 distribute radiation doses to a tumor 115 in discrete multiple beams that diverge or are parallel to each other depending on the type of radiation being distributed. FIG. 1B shows the 3D dose lattice formation 150 with focused photon beams 155 where the radiation beams are focused at dose vertices 160 within a tumor 165. In FIG. 1B, high dose distribution is concentrated over the dose vertices 160 within the tumor 165. Each dose vertex 160 is formed by multiple focused beams 155 and the area surrounding the dose vertices 170 receives a significantly lower dose of radiation than the dose vertices 160. Because dose vertices 160 are generally located within the tumor 165, this tends to minimize the radiation dose to the surrounding normal tissue and therefore minimize toxicity. Whereas in FIG. 1A, 2D Grid radiation therapy, high dose often occurs in regions outside the tumor 110 and then gradually decreases as the radiation moves into and throughout the tumor 115, thus increasing the toxicity of normal tissue. However in 1B, the 3D dose lattice 150, lends to significant reduction in the toxicity to surrounding healthy tissue as the high dose regions are within the tumor.

Figure 2A:
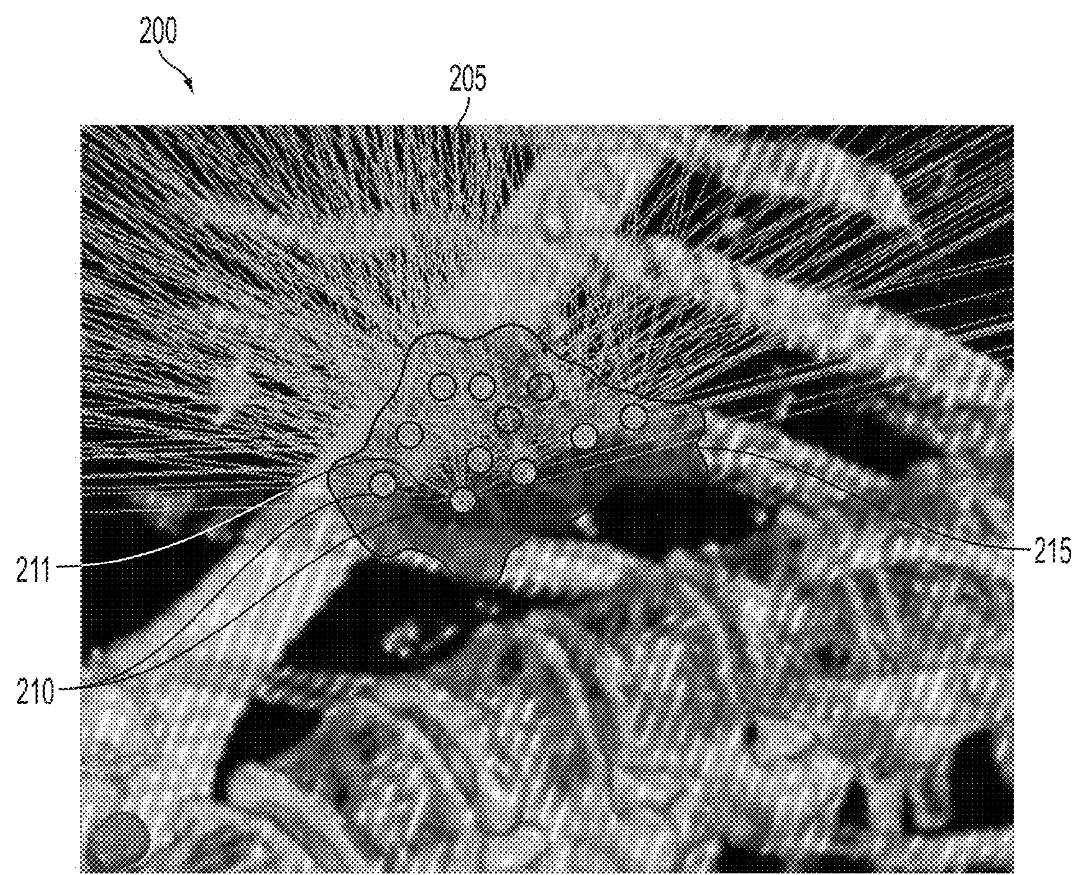
FIGS. 2A and 2B illustrate the 3D dose lattice formation in a pancreatic tumor delivered by non-coplanar focused beams.
Figure 2B:
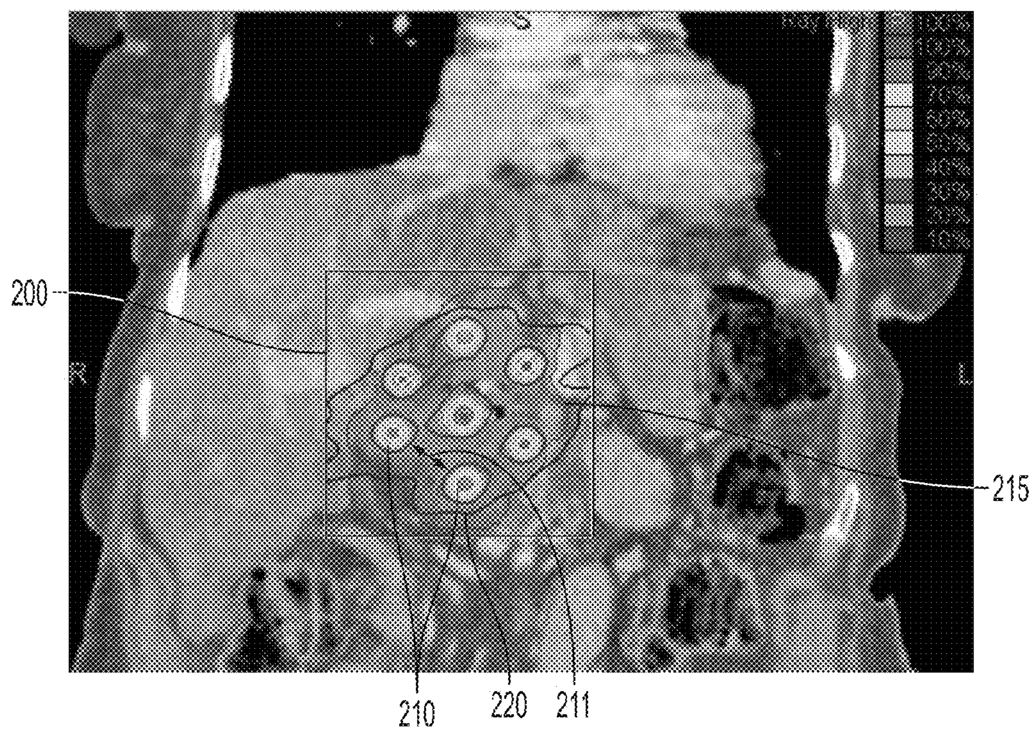
Figure 2C:
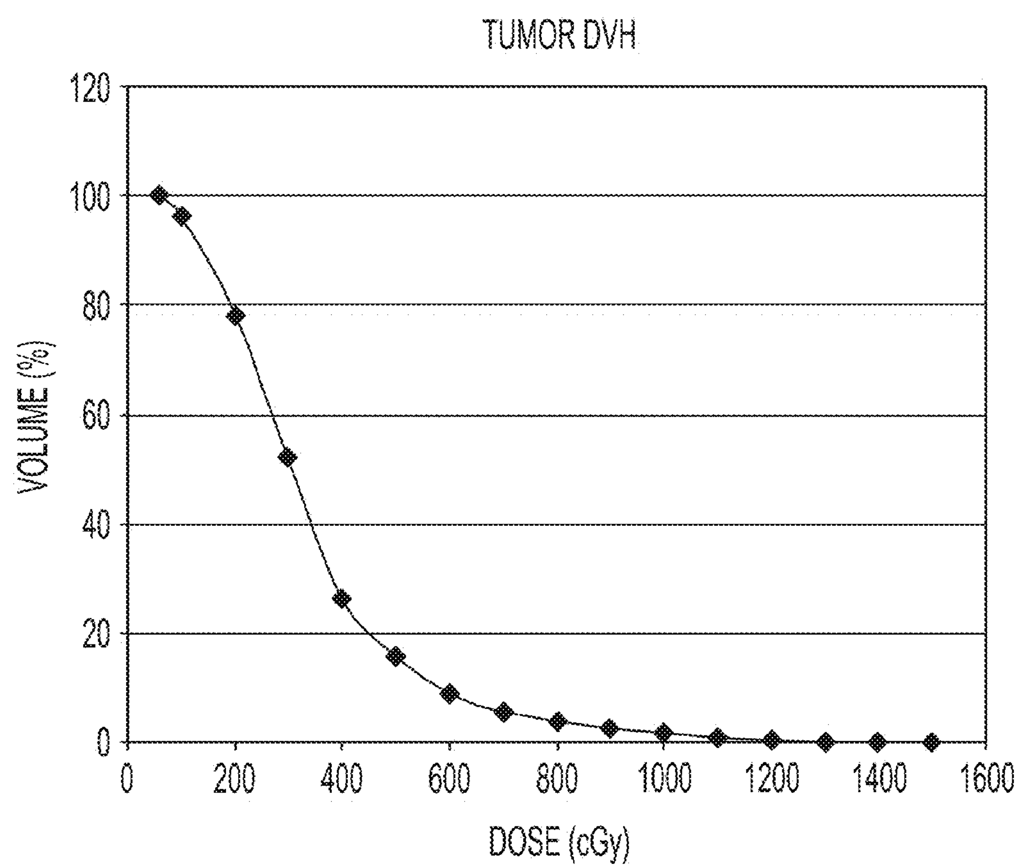
FIG. 2C shows the tumor dose-volume histogram (DVH) indicating a very heterogeneous dose distribution based on the 3D dose lattice formation in FIGS. 2A and 2B.
Figure 2D:
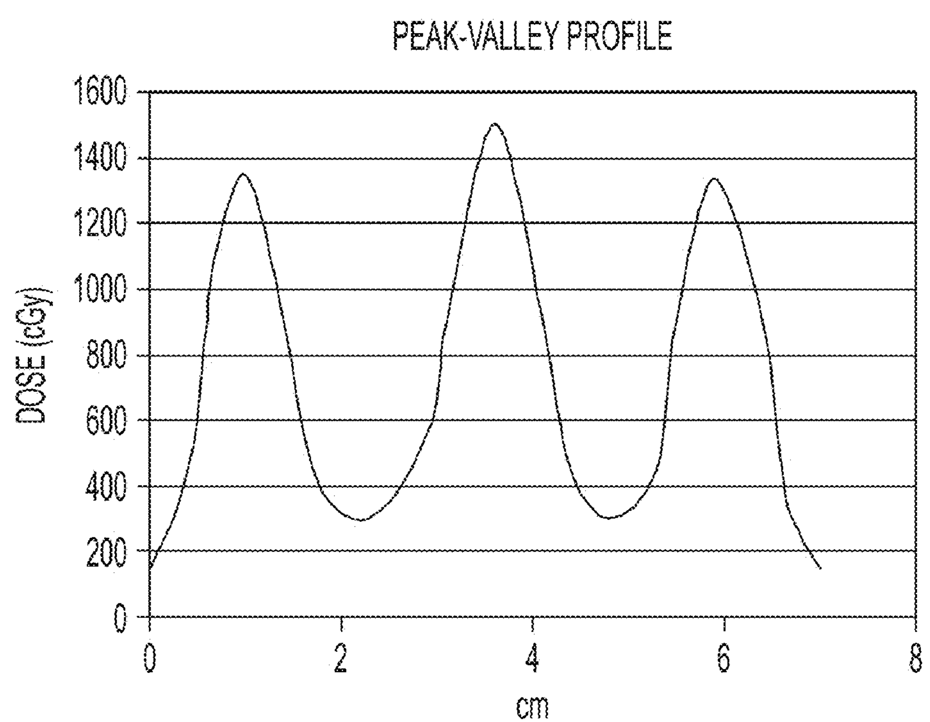
FIG. 2D shows the "Peak-to-Valley" dose profile as a graphical representation of the peak-to-valley profile line shown in FIG. 2B.
Figure 3A:
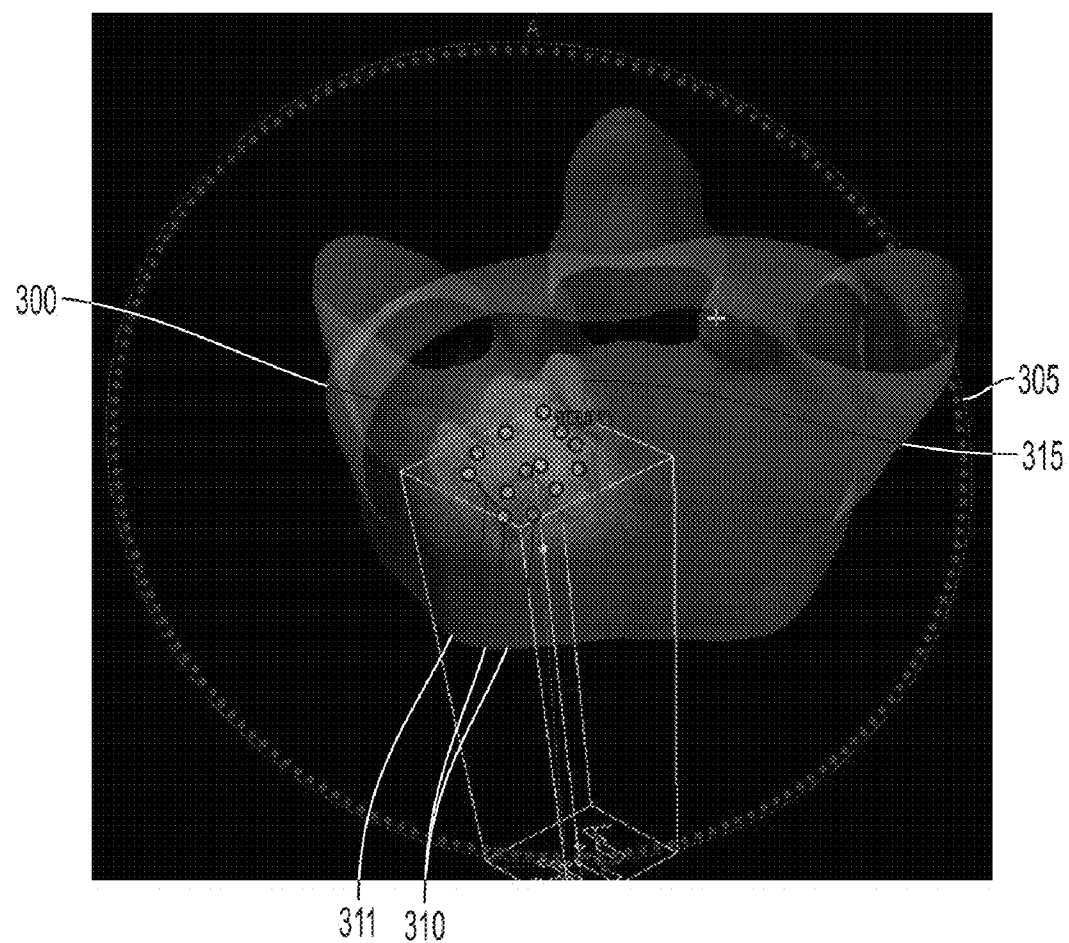
FIGS. 3A and 3B illustrate the 3D dose lattice formation in a lung tumor delivered by a linac using the RapidArc® radiotherapy technology by Varian Medical Systems with 6MV X-rays.
Figure 3B:
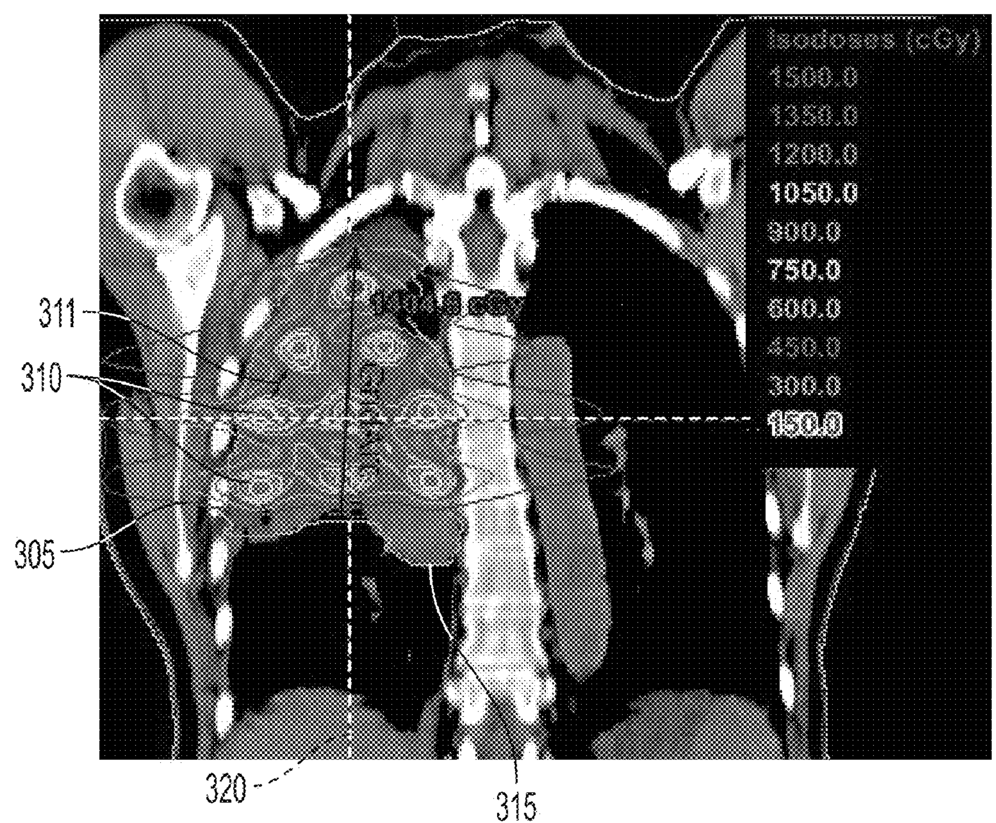
Figure 3C:
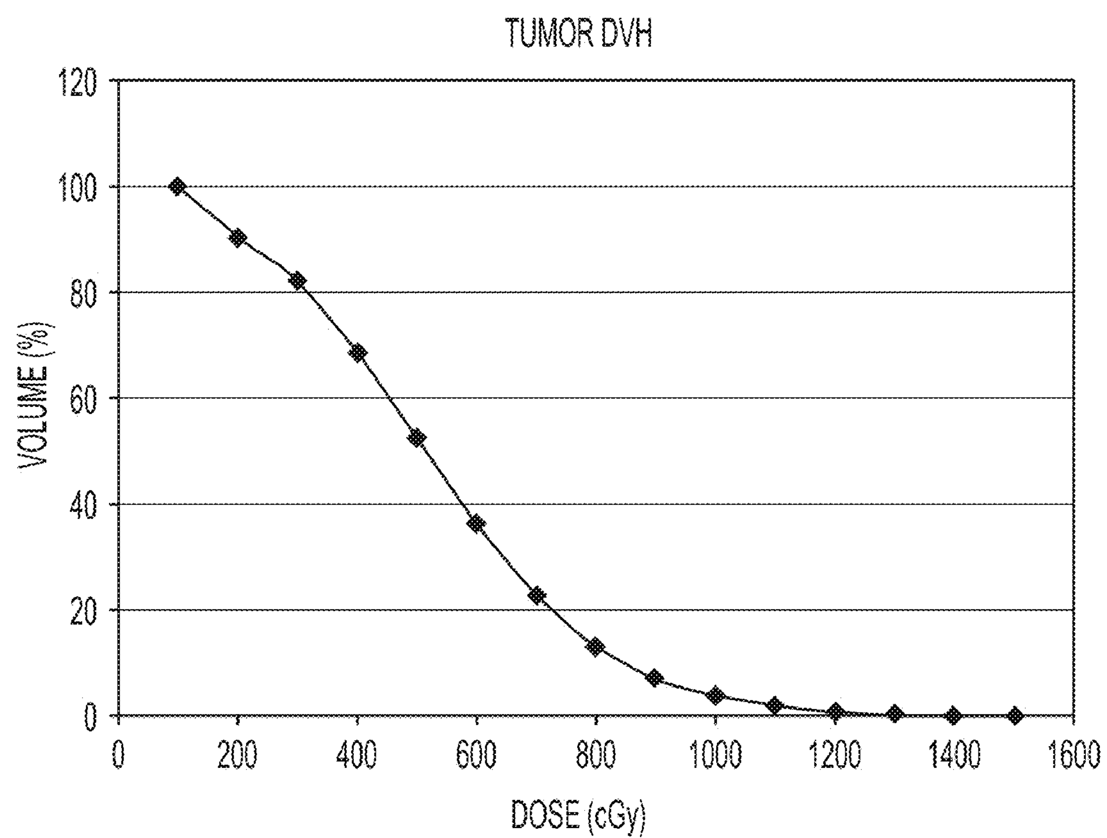
FIG. 3C shows the tumor dose-volume histogram (DVH) indicating a highly heterogeneous dose distribution based on the 3D dose lattice formation in FIGS. 3A and 3B.
Figure 3D:
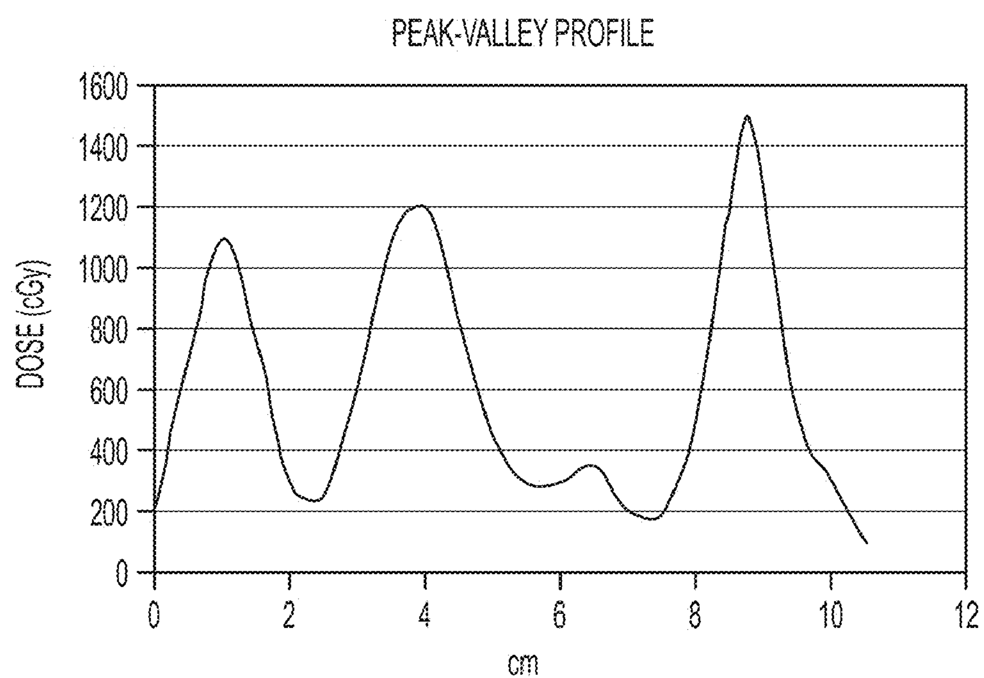
FIG. 3D shows the "Peak-to-Valley" dose profile as a graphical representation of the peak-valley profile line shown in FIG. 3B.
Figure 4:
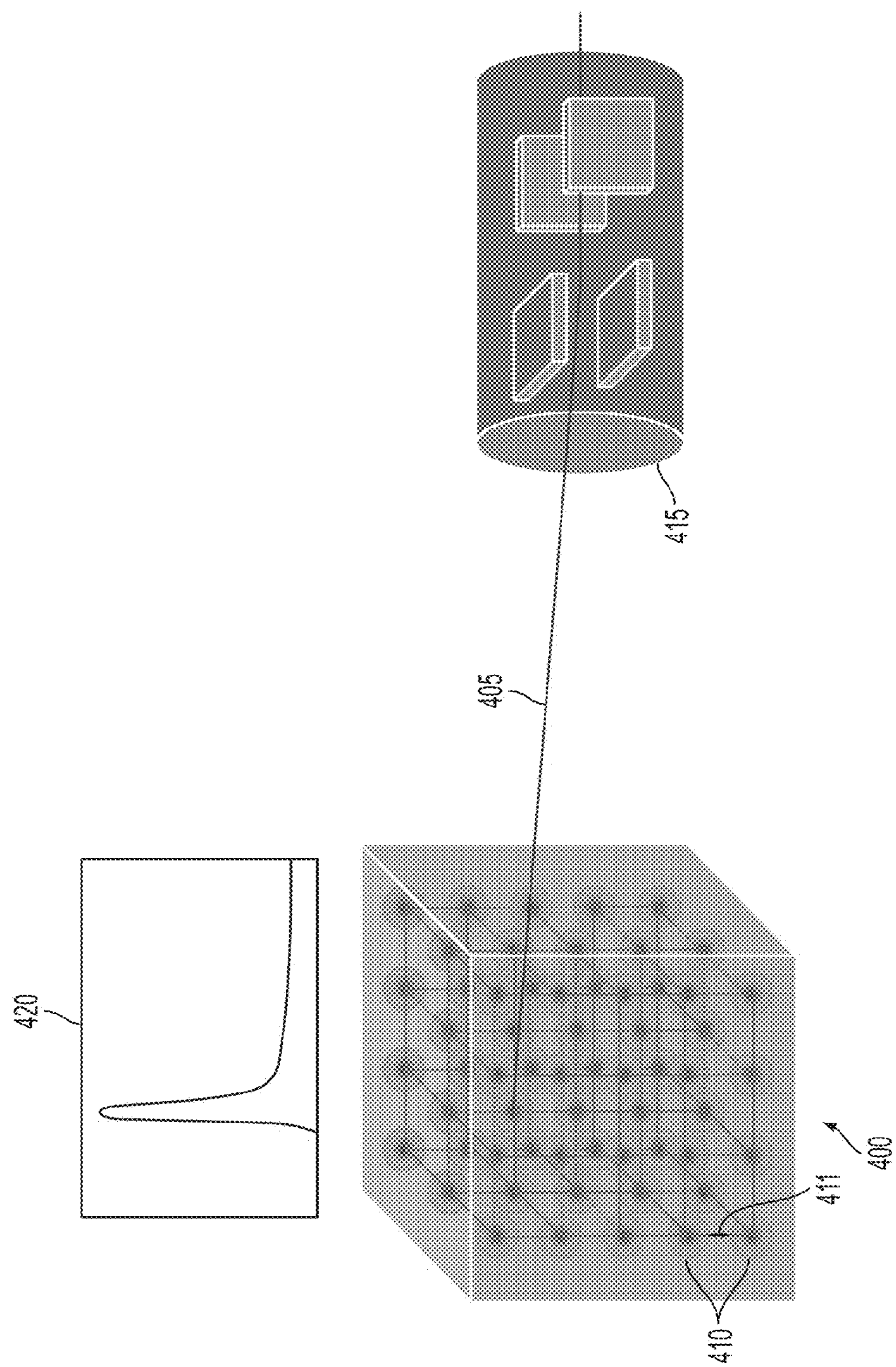
FIG. 4 illustrates the conceptual schematics of 3D dose lattice formation by a heavy charged particle beam with a spot-scanning nozzle and the corresponding Bragg peak.

The 3D dose lattice can be achieved by, but not limited to, three technical approaches: 1) non-coplanar focused beams as illustrated in FIGS. 1B and 2A through 2D; 2) MLC-based IMRT or aperture-modulated arc as illustrated in FIGS. 3A through 3D; and 3) heavy charged particle beam with a spot scanning nozzle as illustrated in FIG. 4. These three technical approaches are further described herein.

Many radiotherapy delivery systems are now capable of delivering multiple focused beams to form highly converged dose distributions. Non-coplanar focused beam techniques are commonly used for stereotactic radiosurgery (SRS) or stereotactic body radiotherapy (SBRT). FIG. 2A shows a 3D dose lattice 200 with non-coplanar focused beams 205 for treatment of a pancreatic tumor 215 as delivered by a Cyberknife™. The Cyberknife is an image-guided robotic radiosurgery system capable of delivering converged beams from a wide range of solid angles. The subject tumor in FIG. 2A is a 185 cc pancreatic mass 215 with eleven (11) dose vertices 210 distributed throughout the tumor 215 volume with about 2.5 cm of separation 211 between dose vertices 210. As shown in FIG. 2A, beams 205 from 40-50 non-coplanar directions with a 7.5 mm collimator converge to form each dose vertex 210. The outcome is a highly heterogeneous dose distribution as demonstrated by the tumor dose volume histogram shown in FIG. 2C, and the oscillating dose distribution of which peak-to-valley dose falls, by way of example, from 1300 cGy to 250-350 cGy as shown in FIG. 2D. It is important to maximize the Δ peak-to-valley dose in order to achieve more robust bystander effect. FIG. 2C shows the resulting dose distribution with 15 Gy prescribed to the maximum within each vertex. FIG. 2B demonstrates that only a small amount of the surrounding normal tissue receives 2-3 Gy and the majority receives much less.

FIGS. 3A through 3D illustrate the 3D dose lattice 300 with a single or multiple arc using a dynamic MLC gantry-linac delivery system to treat a lung tumor 315. The 3D dose lattice 300 can be generated with MLC-based IMRT or aperture-modulated arc technique. Depending on the mechanical flexibility of the MLC used, a 3D dose lattice 300 can be generated with multiple conformal arcs or, in a single aperture modulated arc 305 if inter-digitation is available. FIG. 3A shows a 3D dose lattice 300 as delivered by RapidArc 305 for treatment of a large lung tumor 315 with a volume of 390 cc. The 3D dose lattice 300 in FIG. 3A contains thirteen (13) dose vertices 310 with separation 311 of about 3 cm between dose vertices. FIG. 3C shows the resulting highly heterogeneous dose distribution with 15 Gy prescribed to the maximum within each vertex. FIG. 3B demonstrates that only a small amount of the surrounding normal tissue receives 2-3 Gy and the majority receives much less.

FIG. 4 illustrates the application of 3D dose lattice 400 with a charged particle beam 405 having a spot scanning nozzle 415. Heavy charged particle beams 405, such as proton and carbon ion beams have gained wider interest and use in recent years. Spot-scanning technique has been developed to better conform the beam to treat irregularly shaped tumor volumes to the prescribed dose. A particle beam therapy system with a spot scanning nozzle 415 can be used to efficiently deliver 3D dose lattice radiotherapy. As shown in FIG. 4, a preferred set of the lattice parameters (number and locations 410/separation of the vertices 411) is first determined, depending on the size, shape, and volume of the tumor. The spot-scanning nozzle 415 is then programmed to deliver the Bragg peak 420 (or a minimally spread-out Bragg Peak) to each dose vertex 410. For example, in this embodiment, the spot-scanning nozzle 415 could deliver 15 Gy to a 1 cc volume in less than one (1) minute. The 3D dose lattice using such a delivery system would be both flexible and efficient. Alternatively, a passive filter with an array of small holes can also be used to generate the dose vertices. By changing the energy of heavy charged particle beams, dose vertices can be produced at different depths.

The peak-to-valley dose characteristic is essential to attain the desired therapeutic effect. The peak-to-valley dose profile 220 or 320 is shown in FIGS. 2D and 3D, respectively. The configuration of a 3D dose lattice is comprised of the number, location, and dose of dose vertices. The optimal configuration of a 3D dose lattice can be achieved by manual calculations or by automating the calculations. For example, a generic algorithm using heavy charged particle beams to generate 3D dose lattice is described as follows:

Assume that, 1. a tumor volume is delineated and defined by a 3D boundary designated V; and
2. the desired maximum dose of the lattice is designated $D_{max}$; and
3. the desired minimum dose between dose vertices is designated $D_{min}$; and
4. the maximum dose outside of the tumor volume is designated $D_{exm}$.

The automatic planning process would start with a certain number of dose vertices designated n (n is variable) with each individual vertex designated as i such that the $i^{th}$ vertex is located at position r in the lattice and is designated by $r_i$. This is represented by the vector set $R_L$:

$$R_L(r_1, r_2, r_3, r_4, \ldots r_n)\epsilon V.$$

The Bragg peak dose distribution associated with vertex i is:

$$D_i(r);$$

the composite dose distribution is then $$D(r) = \sum_{i=1}^{n} w_i D_i(r),$$

where $w_i$ is the weighting factor for the $i^{th}$ vertex, forming a scalar set $w_L(w_1, w_2, \ldots w_n)$.

Start iteration to search $R_L$ $(r_i, r_2, r_3, r_4, \ldots r_n)\epsilon V$ and $w_L$ until, $$\sum_i [D(r_i(\sigma)) - D_{max}]^2 \le \delta_{max}, \quad (1)$$

$$\sum_{i,j} [D(r_{i,j})_{min} - D_{min}]^2 \le \delta_{min}, \quad (2)$$

$$D(r \notin V) \le D_{exm}, \quad (3)$$

where, σ is the predefined range within which the maximum dose should fall in at each vertex dose unit; $\delta_{max}$ is the predefined objective threshold for the fitness of $D_{max}$, $\delta_{min}$ is the predefined objective threshold for the fitness of $D_{min}$, and $D(r_{i,j})_{min}$ is the minimum dose along the vector $r_{i,j}=r_i-r_j$.

The objective of the optimization algorithm is to satisfy conditions (1), (2) and (3). This can be achieved by an iteration process until conditions 1, 2, and 3 reaches their global minimum.

The process for achieving the optimization algorithm as described above is not limited to heavy charged particle systems, but may tailored to produce the objective results in photon based radiation therapy systems.

In another embodiment of this invention, the 3D dose lattice formation with a periodic peak-to-valley steep gradient dose distribution can be achieved through multiple focused beams using a radiation therapy system such as a focused-rotating radioisotope assembly. It is understood by one of ordinary skill in the art that this embodiment is not limiting but includes other radiation therapy systems.

It is to be understood, that the subject invention described herein is not limited to the particular embodiments of the invention described herein, as variations of the particular embodiments may be made and still fall within the scope. It is also to be understood that the terminology employed is for the purpose of describing particular embodiments, and is not intended to be limiting.

It should be noted that the methods described herein are not limited to use only with robotic radiosurgery treatment. In alternative embodiments, the methods and apparatus herein may be used in applications within other areas of the medical technology field as well as outside the medical technology field utilizing the application of radiation beams.

The contents of all patents, patent applications, published articles, books, reference manuals and abstracts cited herein are hereby incorporated by reference in their entirety to more fully describe the state of art to which the invention pertains.

As various changes can be made in the above-described subject matter without departing from the scope and the spirit of the invention, it is intended that all subject matter contained in the above description, shown in the accompanying drawings, or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

EQUIVALENTS

Those skilled in the art will recognize, or be able to ascertain using no more than routine experimentation, many equivalents to the specific embodiments of the invention described herein. Such equivalents are intended to be encompassed by the claims.

What is claimed is:

1. A method for delivering radiation to a tumor in a three-dimensional (3D) dose lattice formation using heavy charged particle beams, comprising:

locating a tumor and determining its type, shape, and volume;

determining if the tumor is clinically indicated for 3D lattice radiation treatment;

generating a three-dimensional (3D) dose lattice formation plan by the following algorithm:

delineating and defining the tumor volume by a 3D boundary designated V;

determining the desired maximum dose of the lattice $D_{max}$;

determining the desired minimum dose between dose vertices $D_{min}$;

determining the desired dose outside the tumor volume $D_{exm}$;

setting a variable n as an estimated number of vertices based on the tumor shape and volume;

designating each dose vertex as i such that the $i^{th}$ vertex is located at a position $r_i$ in the 3D lattice;

representing the location of the dose vertices by a vector set $R_L(r_1, r_2, r_3, r_4, \ldots r_n) \in V$;

constructing a Bragg-Peak dose distribution associated with vertex i by $D_i(r)$;

deriving a composite dose distribution using the equation $$D(r) = \sum_{i=1}^{n} w_i D_i(r),$$

where $w_i$ is the weighting factor for the $i^{th}$ vertex, which forms a scalar set $w_L(w_1, w_2, \ldots, w_n)$;

starting iteration to search $R_L$, $(r_1, r_2, r_3, r_4, \ldots r_n) \in V$ and $w_L$ until:

$$1)\ \sum_i [D(r_i(\sigma)) - D_{max}]^2 \leq \delta_{max}, \text{ and}$$

$$2)\ \sum_{i,j} [D(r_{i,j})_{min} - D_{min}]^2 \leq \delta_{min}, \text{ and}$$

$$3)\ D(r \notin V) \leq D_{exm},$$

where σ is a predefined range from the center of vertex, within which the maximum dose, $D_{max}$, should fall; and $r_i(\sigma)$ denotes the vector which displacement from $r_i$ is equal to or less than σ; and $\delta_{max}$ is a predefined objective threshold for the fitness of $D_{max}$; and $\delta_{min}$ is a predefined objective threshold for the fitness of $D_{min}$; and $D(r_{ij})_{min}$ is a minimum dose along the vector $r_{ij}=r_i-r_j$, $(i \neq j)$;

ending iteration; and using resulting vertex positions $(r_1, r_2, r_3, r_4, \ldots r_m)$, where m need not equal n, and $w_L(w_1, w_2, \ldots w_n)$ to deliver the dose lattice with a radiation delivery system.

2. The method in claim 1 wherein a computer program product is used to generate the dose lattice.

* * * * *